United States Patent [19]

Kester

[11] Patent Number: 5,378,631
[45] Date of Patent: Jan. 3, 1995

[54] SEPARATION OF STRONTIUM FROM FECAL MATTER

[75] Inventor: Dianne K. Kester, Idaho Falls, Id.

[73] Assignee: United States Department of Energy, Washington, D.C.

[21] Appl. No.: 195,248

[22] Filed: Feb. 14, 1994

[51] Int. Cl.$^6$ .................. G01N 33/48; G01N 33/50
[52] U.S. Cl. .................................. 436/59; 436/79; 436/155; 436/175
[58] Field of Search .................. 436/59, 79, 155, 175

[56] References Cited

U.S. PATENT DOCUMENTS 5,190,881  3/1993  McKibbin ........................ 436/82

OTHER PUBLICATIONS

Martin, D. B. "Determination of Strontium-89 and -90 in Soil with Total Sample Decomposition", Analytical Chemistry, vol. 51, No. 12, pp. 1968–1972, 1979.

Primary Examiner—David A. Redding
Attorney, Agent, or Firm—Daniel D. Park; Thomas G. Anderson; William R. Moser

[57] ABSTRACT

A method of separating strontium from a sample of biomass potentially contaminated with various radionuclides. After the sample is reduced, dissociated, and carried on a first precipitate of actinides, the first precipitate is removed to leave a supernate. Next, oxalic acid is added to the supernate to cause a second precipitate of strontium and calcium. Then, after separating the second precipitate, nitric acid is added to the second precipitate to cause a third precipitate of strontium. The calcium remains in solution and is discarded to leave essentially the precipitate of strontium.

18 Claims, No Drawings

SEPARATION OF STRONTIUM FROM FECAL MATTER

CONTRACTUAL ORIGIN OF THE INVENTION

The United States Government has rights in this invention pursuant to Contract No. DE-AC07-84ID12435 between the U.S. Department of Energy and Westinghouse Electric Company.

BACKGROUND OF THE INVENTION

The present invention relates to a method of separating strontium, and, more particularly, to a method of separating strontium from a sample of biomass potentially contaminated with various radionuclides.

Radioactive strontium is a radionuclide which represents a hazard to man because of its long half-life and, if ingested, its tendency to be retained in the human body. In the event that radionuclides such as strontium or various actinides are ingested, it is desirable to monitor the discharge or release of these radionuclides from the human body through analysis of fecal matter. In laboratories and other facilities where potential for radionuclide contamination exists, fecal analysis for strontium is routinely conducted for individuals who are terminating from their position or are suspected of having been contaminated with radionuclides.

Methods for separating and analyzing radioactive actinides from a biomass sample are well known and have been extensively developed for the U.S. Department of Energy. These methods, described in the Department's internal procedure, USDOE, RESL/ID, A-16, 1981, as well as in U.S. Pat. No. 5,190,881, involve the use of an iron phosphate precipitation step to separate actinides from a solution, or supernate. However, there are no established procedures for the separation of strontium from a biomass sample wherein an iron phosphate precipitation step is involved.

Various strontium removal methods are known in the prior art. But these methods, usually used to remove strontium from nuclear fuel wastes, are not well adapted to the separation of small amounts of strontium from a small biomass sample to conduct radioactive analysis. Other separation methods require the use of highly toxic fuming nitric acid which is hazardous and difficult to dispose of.

In view of the foregoing, the general object of this invention is to provide a method of separating strontium from a sample of biomass that is efficient and which reduces the amount of hazardous waste that is generated.

Additional objects, advantages and novel features of the invention will become apparent to those skilled in the art upon examination of the following and by practice of the invention.

SUMMARY OF THE INVENTION

To achieve the foregoing and other objects, this invention provides a method of separating strontium from a sample of biomass potentially contaminated with various radionuclides. After the sample is reduced, dissociated, and carried on a first precipitate of actinides, the first precipitate is removed to leave a supernate. Next, oxalic acid is added to the supernate to cause a second precipitate of strontium and calcium. Then, after separating the second precipitate, nitric acid is added to the second precipitate to cause a third precipitate of strontium. The calcium remains in solution and is discarded to leave essentially only the third precipitate of strontium.

To separate the strontium from its yttrium daughter, water and Diethylenetriamine pentaacetic acid (DTPA) is added to the third precipitate to dissolve it. Then, sodium sulfate ($Na_2SO_4$) is added to cause a fourth precipitate of strontium while leaving the yttrium in solution. Finally, the solution is discarded to leave the fourth precipitate essentially free of yttrium.

To determine the strontium concentration of the sample, the fourth precipitate is first placed in solution using DTPA and then allowed to stand for a seven day ingrowth period wherein yttrium-90 is allowed to form. Then, after separating yttrium from strontium using conventional separation methods, the yttrium is counted to determine the strontium concentration.

DESCRIPTION OF THE PREFERRED EMBODIMENT

The invention is directed to the separation of strontium from a sample of biomass suspected of containing radionuclides. In the embodiment disclosed herein, a fecal sample is reduced, dissociated, and carried on a first precipitate of actinides to leave a supernate. Next, oxalic acid is added to the supernate to cause a precipitate of strontium and calcium. Then, nitric acid is added to the precipitate to cause a precipitate of strontium while the calcium is left in solution.

As in previously known procedure for fecal dissolution and reduction, the fecal sample is dried on a hot plate, then ignited and muffled in a furnace at 550 C. for sixteen hours. After adding an appropriate strontium-85 tracer to the sample ash, the ash is treated with hydrochloric, nitric, perchloric and hydrofluoric acids to remove organic and siliceous material. The slurry of salts remaining are taken through a pyrophosphate fusion on a hot plate to facilitate the complete dissolution in 2 Molar (M) Hcl. Iron(III) is added to act as a carrier. A reduction is performed using ascorbic acid and titanium trichloride. The pH of the sample is carefully adjusted to about 3.0–3.5 using ammonium hydroxide which precipitates iron(II) phosphate. The actinides, including americium, reduced uranium and plutonium, are carried on the iron phosphate precipitate, while the strontium remains in the solution, or supernate.

After the iron phosphate precipitate is removed from the supernate, a stable strontium and calcium carrier is added to the supernate to facilitate further precipitation. In the preferred embodiment, the strontium carrier is obtained by dissolving $Sr(NO_3)_2$ in 4M nitric acid, while the calcium carrier is obtained by dissolving $CaCl_2$ in water. Next, a saturated solution of oxalic acid is added to the supernate to form calcium and strontium oxalate precipitates. To facilitate the precipitation of strontium and calcium, ammonium hydroxide is added to the solution to raise its pH to about 4. Also, the solution is heated to boiling on a hot plate while continuously stirring. After allowing the mixture to stand overnight, the mixture is then centrifuged, and the resulting supernate is removed. To save time, the entire mixture may be centrifuged immediately after allowing the mixture to cool to room temperature.

To separate strontium from calcium, concentrated nitric acid is added to the remaining oxalate precipitate, and then the entire mixture is brought to boiling. The more hazardous "fuming" nitric acid is not required for the invention, and consequently, any material handling and waste disposal requirements are simplified. By the addition of the concentrated nitric acid, the oxalate precipitate is dissolved and metastasizes into a strontium nitrate precipitate, while leaving the more soluble calcium nitrate in solution. After boiling, the mixture is cooled in a cold water bath and is allowed to remain cold for about 30±10 minutes to decrease the solubility of the strontium nitrate precipitate. Next, after centrifuging the mixture and discarding the supernate, the strontium nitrate precipitate is dissolved in 15±5 mL of water. If any residual precipitate remains after dissolution in water, the solution is centrifuged to remove the residual precipitate. To insure that essentially all strontium has been removed, the residual precipitate is checked for $^{85}Sr$ using a NaI $\gamma$ detector.

If $^{85}Sr$ is detected in the residual precipitate, the precipitate is dissolved in 1.3M Diethylenetriamine pentaacetic acid (DTPA) to further dissociate strontium from the precipitate. To promote dissolution of strontium, the solution needs to be basic. To test for basicity, 5±1 drops of m-Cresolsulfonephthalein (meta-Cresol Purple, or MCP) indicator is added to the solution. The solution should turn purple. However, if the solution is not purple, or basic, 18M sodium hydroxide is added until the if solution turns purple. The solution is then heated in a hot water bath for 5±2 minutes and vortexed to completely dissolve any remaining or additional precipitates. If any precipitation remains, the solution should be further centrifuged to remove the precipitation. This second residual precipitation may again be checked for $^{85}Sr$ using a NaI detector to insure that no strontium remains in the second residual precipitation. The strontium/DTPA solution is then added to the strontium/water solution from the previous step.

If $^{85}Sr$ was not detected in the first residual precipitate, the DTPA is added directly to the strontium/water solution using the MCP indicator and sodium hydroxide as described above. If any extraneous precipitation occurs, the precipitation is removed after centrifuging.

At this point, yttrium-90, which is a daughter of strontium-90, is separated from the strontium. Since the yttrium-90 daughter has a higher energy data than the strontium-90 mother, it is normally desirable to count the yttrium-90 at the end of a predetermined in-growth period in which the yttrium-90 is allowed to form. Accordingly, to insure that no yttrium remains in the strontium/DTPA solution at the beginning of the in-growth period, all yttrium must be removed.

There are various known methods of separating strontium from its yttrium daughter. In the embodiment of the invention described herein, 5±1 mL of 1.4M sodium sulfate ($Na_2SO_4$) is added to the strontium/DTPA solution. This step, by precipitating $SrSO_4$, separates the yttrium daughter from the strontium. To facilitate the precipitation of $SrSO_4$, 5±1 mL of glacial acetic acid is initially added to the solution. Gradually, more glacial acetic acid is added until the pH of the solution reaches 4.0±0.2. Thereafter, the solution is heated in a boiling water bath for at least 5 minutes and the solution centrifuged for 10±5 minutes to separate the strontium precipitate from the supernate. The in-growth period of the yttrium-90 daughter begins at this point, so the date and time of when the supernate is discarded is carefully recorded.

After discarding the supernate, 5±2 mL of 1.3M DTPA is added to the strontium precipitate to place it in a solution form for counting. To enhance the dissolution, 5±2 mL of MCP is added to the solution and 18M sodium hydroxide is added a drop at a time until the purple endpoint of the MCP indicator is reached. If all of the strontium precipitate has not dissolved at this point, add more DTPA in mL aliquot up to a 10 mL total.

Any time during the in-growth period, a count can be made to determine the $^{85}Sr$ tracer concentration within the solution. By comparing the $^{85}Sr$ concentration within the solution with that of a control sample, the quantity of the $^{85}Sr$ lost in the separation procedure can be determined to estimate the yield of the $^{90}Sr$ recovery. After counting, the solution is diluted to 25±5 mL with water and the in-growth period in continued. The period should last for at least seven days to achieve over 65% secular equilibrium.

After the seven day in-growth period, yttrium-90 can be separated from the strontium using a number of conventional, well known separation procedures. In the invention described herein, the yttrium is separated by precipitating yttrium hydroxide using sodium hydroxide, while leaving the strontium in the DTPA solution. A further purification may involve the extraction of yttrium into a 50/50 solution of Di-phosphoric acid (HDEHP) and dodecane out of a weak HCl solution. The yttrium is then back extracted into a strong HCl solution and precipitated as a final oxalate precipitate. The final yttrium oxalate precipitate is then counted using a gas flow proportional low background beta counter to determine the quantity of the strontium-90.

Alternate embodiments of the invention includes the application of the foregoing strontium separation procedure to various biomass or other samples including urine, vegetation, animal or human tissue, soil and water. The procedure described herein can be used on almost any sample so long as an iron phosphate precipitation step or its equivalent is included in the separation process to remove actinides while leaving strontium in the supernate.

The foregoing description of a preferred embodiment of the invention has been presented for purposes of illustration and description. It is not intended to be exhaustive or to limit the invention to the precise form disclosed. As stated above, the procedure is not limited to the analysis of fecal samples only. The procedure is easily adaptable to various other samples which may require strontium analysis. The embodiment described herein explains the principles of the invention so that others skilled in the art may practice the invention in various embodiments and with various modifications as suited to the particular use contemplated. It is intended that the scope of the invention be defined by the claims appended hereto.

The embodiments of this invention in which an exclusive property or privilege is claimed are defined as follows:

1. A method of separating strontium from a sample of biomass potentially contaminated with various radionuclides, said sample having been reduced, dissociated, and carried on a first precipitate of actinides, comprising the steps of:

removing the first precipitate to leave a supernate containing strontium;

adding oxalic acid to the supernate to cause a second precipitate of strontium and calcium;

separating the second precipitate from the supernate;

adding nitric acid to the second precipitate to cause a third precipitate of strontium while leaving the calcium in solution; and separating the third precipitate from the solution.

2. The method of claim 1 wherein the second and third precipitates are respectively separated from the solution by centrifuging.

3. The method of claim 1 including the step of adding a stable strontium and calcium carrier to the supernate after removing the first precipitate.

4. The method of claim 1 including the step of adding ammonium hydroxide to the supernate after adding oxalic acid to facilitate precipitation of strontium and calcium.

5. The method of claim 1 including the step of cooling the third precipitate and the solution in a cold water bath before separating said third precipitate from said solution.

6. The method of claim 1 including the steps of:
boiling the supernate after addition of the oxalic acid; and boiling the solution after addition of the nitric acid.

7. The method of claim 1 wherein the nitric acid is concentrated nitric acid.

8. The method of claim 1 wherein the sample of biomass is selected from the group consisting of urine, feces, vegetation, tissue, soil and water.

9. The method of claim 1 including the steps of dissolving the third precipitate in water and centrifuging the solution to remove residual precipitates.

10. The method of claim 9 including the step of adding Diethylenetriamine pentaacetic acid (DTPA) and sodium hydroxide to the residual precipitates to further separate strontium from said residual precipitates.

11. The method of claim 1 including the steps of:
adding water and Diethylenetriamine pentaacetic acid (DTPA) to the third precipitate to dissolve said third precipitate to form a strontium/DTPA solution;
adding sodium sulfate ($Na_2SO_4$) to the strontium/DTPA solution to cause a fourth precipitate of strontium while leaving yttrium in solution;
discarding the solution to leave the fourth precipitate essentially free of yttrium; and
adding DTPA to the fourth precipitate to place said fourth precipitate in solution.

12. The method of claim 11 including the step of adding sodium hydroxide to the third precipitate to promote dissolution of said third precipitate.

13. The method of claim 11 including the step of adding glacial acetic acid to the strontium/DTPA solution to promote the precipitation of strontium sulfate ($SrSO_4$).

14. The method of claim 11 including the step of counting strontium-85 in the fourth precipitate solution to calculate yield of the strontium-90 recovery.

15. The method c,f claim 11 including the step of standing the fourth precipitate solution for a seven day in-growth period wherein yttrium-90 is allowed to form.

16. The method c,f claim 15 including the steps of separating yttrium from strontium after the seven day in-growth period and counting the yttrium to determine the strontium concentration.

17. A method of separating strontium from a sample of biomass potentially contaminated with various radionuclides, said sample having been reduced, dissociated, and carried on a first precipitate of actinides, comprising the steps of:
removing the first precipitate to leave a supernate containing strontium;
adding oxalic acid to the supernate to cause a second precipitate of strontium and calcium;
separating the second precipitate from the supernate;
adding nitric acid to the second precipitate to cause a third precipitate of strontium while leaving the calcium in solution;
separating the third precipitate from the solution;
adding water and Diethylenetriamine pentaacetic acid (DTPA) to the third precipitate to dissolve said third precipitate to form a strontium/DTPA solution;
adding sodium sulfate ($Na_2SO_4$) to the strontium/DTPA solution to cause a fourth precipitate of strontium while leaving yttrium in solution;
discarding the solution to leave the fourth precipitate essentially free of yttrium; and
adding DTPA to the fourth precipitate to place said fourth precipitate in solution.

18. A method of separating strontium from a sample of biomass potentially contaminated with various radionuclides, said sample having been reduced, dissociated, and carried on a first precipitate of actinides, comprising the steps of:
removing the first precipitate to leave a supernate containing strontium;
adding oxalic acid to the supernate to cause a second precipitate of strontium and calcium;
separating the second precipitate from the supernate;
adding nitric acid to the second precipitate to cause a third precipitate of strontium while leaving the calcium in solution;
separating the third precipitate from the solution;
adding water and Diethylenetriamine pentaacetic acid (DTPA) to the third precipitate to dissolve said third precipitate to form a strontium/DTPA solution;
adding sodium sulfate ($Na_2SO_4$) to the strontium/DTPA solution to cause a fourth precipitate of strontium while leaving yttrium in solution;
discarding the solution to leave the fourth precipitate essentially free of yttrium;
adding DTPA to the fourth precipitate to place said fourth precipitate in solution;
standing the fourth precipitate solution for a seven day in-growth period wherein yttrium-90 is allowed to form;
separating yttrium from strontium after the seven day in-growth period; and
counting the yttrium to determine the strontium concentration.

* * * * *